(12) United States Patent
Kang et al.

(10) Patent No.: US 8,039,803 B2
(45) Date of Patent: Oct. 18, 2011

(54) PHASE CONTRAST IMAGING METHOD AND APPARATUS

(75) Inventors: Kejun Kang, Beijing (CN); Zhiqiang Chen, Beijing (CN); Li Zhang, Beijing (CN); Yingxin Wang, Beijing (CN); Ziran Zhao, Beijing (CN); Yuanjing Li, Beijing (CN); Yinong Liu, Beijing (CN); Zhifeng Huang, Beijing (CN); Yuxiang Xing, Beijing (CN)

(73) Assignees: Tsinghua University, et al., Beijing (CN); Nuctech Company Limited, Beijing (CN)

( * ) Notice: Subject to any disclaimer, the term of this patent is extended or adjusted under 35 U.S.C. 154(b) by 0 days.

(21) Appl. No.: 12/920,161

(22) PCT Filed: Feb. 16, 2009

(86) PCT No.: PCT/CN2009/000154
§ 371 (c)(1),
(2), (4) Date: Oct. 7, 2010

(87) PCT Pub. No.: WO2009/109098
PCT Pub. Date: Sep. 11, 2009

(65) Prior Publication Data
US 2011/0024624 A1    Feb. 3, 2011

(30) Foreign Application Priority Data

Mar. 5, 2008    (CN) .......................... 2008 1 0101353

(51) Int. Cl.
*G01J 5/02* (2006.01)

(52) U.S. Cl. .................................................. 250/341.1

(58) Field of Classification Search .................. 250/330, 250/331–335, 338.1–338.4, 341.1–341.8
See application file for complete search history.

(56) References Cited

U.S. PATENT DOCUMENTS

| | | | |
|---|---|---|---|
| 2004/0105100 A1* | 6/2004 | Shirley | 356/603 |
| 2006/0029941 A1 | 2/2006 | Koo et al. | 435/6 |

(Continued)

FOREIGN PATENT DOCUMENTS

CN    1560613    1/2005

(Continued)

OTHER PUBLICATIONS

Ranalli et al., "Diffraction gratings and binary temporal holograms as optical delay line diffractive arrays," 1995, Optics Communications, vol. 117, pp. 219-222.*

(Continued)

*Primary Examiner* — David P. Porta
*Assistant Examiner* — Kiho Kim
(74) *Attorney, Agent, or Firm* — Westman, Champlin & Kelly, P.A.

(57) ABSTRACT

A method for phase contrast imaging comprises: illuminating an object by terahertz radiation such that the terahertz radiation interacts with the object; illuminating a diffraction grating by the terahertz radiation that has interacted with the object; translating the diffraction grating along the direction of the grating wave vector, to measure, for each of different grating positions, an intensity distribution of the terahertz radiation that has interacted with the object and with the grating in a diffraction field; and retrieving a phase contrast image of the object from the intensity distributions. An apparatus for phase contrast imaging is also provided.

15 Claims, 2 Drawing Sheets

U.S. PATENT DOCUMENTS

2006/0231625 A1* 10/2006 Cumming et al. ............ 235/454
2009/0200472 A1* 8/2009 Gregory ................... 250/339.07

FOREIGN PATENT DOCUMENTS

| CN | 2833576 | 11/2006 |
|---|---|---|
| CN | 2874476 | 2/2007 |
| CN | 1940542 | 4/2007 |
| CN | 200996980 | 12/2007 |
| JP | 2007248100 | 9/2007 |

OTHER PUBLICATIONS

Jiang et al., "Spatio-temporal Imaging of THz pulses," 1998, IEEE Terahertz Electronics Proceedings, 1998. THz Ninety Eight. 1998 IEEE Sixth International Conference on, pp. 94-97.*

Search Report from PCT/CN2009/000154, dated May 28, 2009.

Written Opinion (ISA 237) from PCT/CN2009/000154, dated May 28, 2009.

"Imaging with Terahertz Waves", by B.B. Hu et al., *Optics Letters*, vol. 20, No. 16, 1995, pp. 1716-1718.

"Phase-Sensitive X-Ray Imaging", by R. Fitzgerald, *Physics Today*, 2000, pp. 23-26.

"X-Ray Phase Imaging with Single Phase Grating", by Y. Takeda, *Japanese Journal of Applied Physics*, vol. 4, No. 3, 2007, pp. L89-L91.

"Far Infrared Imagery", by T.S. Hartwick et al., *Applied Optics*, vol. 15, No. 8, 1976, pp. 1919-1922.

Terahertz, *ACTA Photonica Sinica*, vol. 35, No. 8, 2006, pp. 1171-1174 (English Abstract).

* cited by examiner

PHASE CONTRAST IMAGING METHOD AND APPARATUS

CROSS-REFERENCE TO RELATED APPLICATION

This Application is a Section 371 National Stage Application of International Application No. PCT/CN2009/000154, filed Feb. 16, 2009, the contents of which are hereby incorporated by reference in their entirety.

FIELD OF THE INVENTION

The invention generally relates to the terahertz imaging field, and more particularly, to a method and an apparatus for improving imaging contrast and spatial resolution by deriving phase contrast information of an object illuminated by terahertz radiation using a diffraction gating.

DESCRIPTION OF THE PRIOR ART

Terahertz (THz, i.e. $10^{12}$ Hz) radiation usually refers to the electromagnetic radiation with a frequency between 0.1~10 THz, which is in the far infrared wave band of the electromagnetic wave spectrum. Compared with conventional imaging technologies such as visible light or X-ray imaging, the terahertz imaging has many complementary features. The terahertz electromagnetic wave can easily penetrate dielectric materials of no polarity or weak polarity, and thus can be used in non-destructive detection of such materials or inspection of objects hidden by them. The photon energy of the terahertz radiation is low and will not cause light-induced ionization or damage, and thus is safer for imaging of biological samples. The terahertz spectroscopic imaging technology based on measurement of spectroscopic information is capable of analyzing categories and components of a substance. Therefore, the terahertz imaging is a safe and effective technology for non-destructive detection, which has a broad application prospect in fields such as material science, biomedicine, and security inspection.

The conventional terahertz imaging (Document 1: T. S. Hartwick, at al. Far infrared imagery. *Applied Optics,* 1976, 15(8): 1919-1922) utilizes absorption and attenuation characteristics of a substance to the terahertz radiation to reflect intensity distribution information of the terahertz radiation after interacting with the object, that is, variations in amplitude. For a substance of weak absorption, the attenuation degree of the terahertz radiation will be very small, and the contrast of a resultant image is bad such that the internal structure of the object is difficult to be identified. However, variations in refractive indices of mediums through which the electromagnetic wave passes will cause phase variations (phase shifts) of the electromagnetic wave, the degree of which is larger that that of the attenuation. Therefore, detecting the phase shift information is more effective. If such information can be captured to obtain a phase contrast image of the object, the contrast and resolution of imaging of the substance of weak absorption will be substantially improved (Document 2: X I Zaijun at al, Two dimensional transmissive terahertz wave time domain spectrum imaging research, *ACTA PHOTONICA SINICA,* 2006, 35(8): 1171-1174). Document 3 (B. B. Hu and M. C. Nuss. Imaging with terahertz waves. *Optics Letters,* 1995, 20(16): 1716-1718) discloses an imaging system for measuring both amplitude and phase information of the terahertz radiation. The system uses a pulsed light source, coherently detects the time domain wave form of the terahertz pulse based on the terahertz time domain spectroscopy (THz-TDS) technology, and obtains the amplitude and phase of the spectrum by means of Fourier transformation, which carry the absorption and refraction information of the object to the terahertz radiation. Recent terahertz time domain spectroscopic imaging systems are developed essentially on this basis, and have a common defect of complex system structure and high cost due to the pump—probe scheme adopted.

In the X-ray imaging field, the phase contrast imaging technology has been vigorously developed. The phase contrast imaging technology expands the range of substances detectable by the X-ray to light element substances of weak absorption, and enhances the spatial resolution from millimeter order to micrometer order, or even to sub-micrometer order. There have been developed three different types of X-ray phase contrast imaging technologies (Document 4: R. Fitzgerald. Phase-sensitive X-ray imaging. *Physics Today,* 2000, 53(7): 23-26), including interference measurement, diffraction enhancement, and in-line imaging, which can be referenced by the terahertz radiation phase contrast imaging. Document 5 (Y. Takeda, et al. X-ray phase imaging with single phase grating. *Japanese Journal of Applied Physics,* 2007, 46(3): L89-L91) discloses a laboratory system for X-ray phase contrast imaging with a single phase grating. When an object of weak absorption, with a phase grating disposed behind, is illuminated with partly coherent X-ray, the periodic intensity pattern caused by the Talbot effect in the diffraction field of the grating will be distorted. The intensity distribution is recorded by a CCD (charge coupled device) detector, and then a phase contrast image of the object can be obtained by a phase retrieval algorithm. This method has a strict requirement on the coherence of the light source and the resolution of the CCD, but the system structure is very simple. By contrast, the wavelength of the terahertz radiation is much longer, and a corresponding grating period is in an order of millimeter. Consequently, the resolution of a suitable detector can also be in this order. Gratings of such size are easy to manufacture, and the coherence of continuous-wave terahertz sources is easy to ensure. Therefore, it is possible to perform terahertz radiation phase contrast imaging using a single grating.

SUMMARY OF THE INVENTION

In order to overcome the defects of the prior art, there is provided a method and an apparatus for terahertz radiation phase contrast imaging, where a phase contrast image of an object is created from phase variation information of the terahertz radiation after it interacts with the object obtained by means of a diffraction grating.

According to an aspect of the present invention, there is provided a method for phase contrast imaging using a diffraction grating, comprising steps of: illuminating an object by coherent terahertz radiation such that the terahertz radiation interacts with the object; illuminating the grating by the terahertz radiation that has interacted with the object; translating the diffraction grating along the direction of the grating wave vector to measure, for each different grating positions, an intensity distribution of the terahertz radiation that has interacted with the object and with the grating in a diffraction field; and retrieving a phase contrast image of the object from the intensity distributions.

Preferably, the step of illuminating the grating by the terahertz radiation that has interacted with the object comprises: illuminating the grating by the terahertz radiation that has passed through the object.

Preferably, the step of illuminating the grating by the terahertz radiation that has interacted with the object comprises: illuminating the grating by the terahertz radiation that has been reflected by the object.

Preferably, the diffraction grating is translated within a distance of one period along the direction of the wave vector of the diffraction grating, such that for each particular grating position, a plane in the diffraction field of the grating, in which a contrast of diffraction fringes is relatively high, is selected for measuring the intensity distribution of the terahertz radiation.

Preferably, the intensity distribution of the terahertz radiation is measured point by point by a single point type detector in a manner of raster scanning.

Preferably, the intensity distribution of the terahertz radiation is measured directly by an array detector.

Preferably, the step of retrieving the phase contrast image of the object from the intensity distributions comprises: retrieving a phase distribution of a grating incident field in a plane perpendicular to an incident direction from the periodic intensity pattern and diffraction characteristic of the grating; and creating the phase contrast image of the object from the phase distribution.

According to another aspect of the present invention, there is provided an apparatus for phase contrast imaging, comprising: a terahertz radiation emitter for generating terahertz radiation, which illuminates an object to interact with the object; a diffraction grating, which is illuminated by the terahertz radiation that has interacted with the object; a terahertz radiation detector for measuring, for each of different grating positions, an intensity distribution of the terahertz radiation that has interacted with the object and with the grating in a diffraction field; and a data collecting and processing system for retrieving a phase contrast image of the object from the intensity distributions.

Preferably, the apparatus for phase contrast imaging further comprises: a collimating portion arranged at an output side of the terahertz radiation emitter for collimating the terahertz radiation into a parallel beam.

Preferably, the collimating portion is a terahertz lens or a parabolic mirror.

Preferably, the apparatus for phase contrast imaging further comprises: a translating device for translating the grating at equivalent pitches along the direction of the grating wave vector.

Preferably, the translating device translates the diffraction grating within a distance of one period along the direction of the wave vector of the diffraction grating, such that for each particular grating position, a plane in the diffraction field of the grating, in which a contrast of diffraction fringes is relatively high, is selected for measuring the intensity distribution of the terahertz radiation by the terahertz radiation detector.

Preferably, the terahertz radiation detector is a single point type detector for measuring the intensity distribution of the terahertz radiation point by point in a manner of raster scanning.

Preferably, the terahertz radiation detector is an array detector for measuring the intensity distribution of the terahertz radiation directly.

Preferably, the data collecting and processing system retrieves a phase distribution of a grating incident field in a plane perpendicular to an incident direction from the periodic intensity pattern and diffraction characteristic of the grating, and creates the phase contrast image of the object from the phase distribution.

The present invention has the following advantages over the prior art by adopting the above method and apparatus.

1) The present invention enables phase contrast imaging in a continuous wave terahertz system, and improves contrast and spatial resolution for imaging of an objection of weak absorption.

2) According to the present invention, the phase variation information of the terahertz radiation after it has interacted with the object is extracted, such that the system is compact in structure and easy to be operated.

3) The intensity measurement of the continuous wave terahertz radiation does not need scanning the wave form in time domain, such that it is possible to obtain the phase distribution information rapidly.

BRIEF DESCRIPTION OF THE DRAWINGS

The above features and advantages of the present invention will become more apparent from the following description with reference to the figures, wherein.

DETAILED DESCRIPTION OF THE PREFERRED EMBODIMENTS

Preferred embodiments of the present invention will be explained in detail with reference to the figures. For purpose of clarity and conciseness, detailed descriptions on known functions and structures incorporated therein will be omitted, in order to avoid obscuring the subject matters of the present invention.

Figure 1:
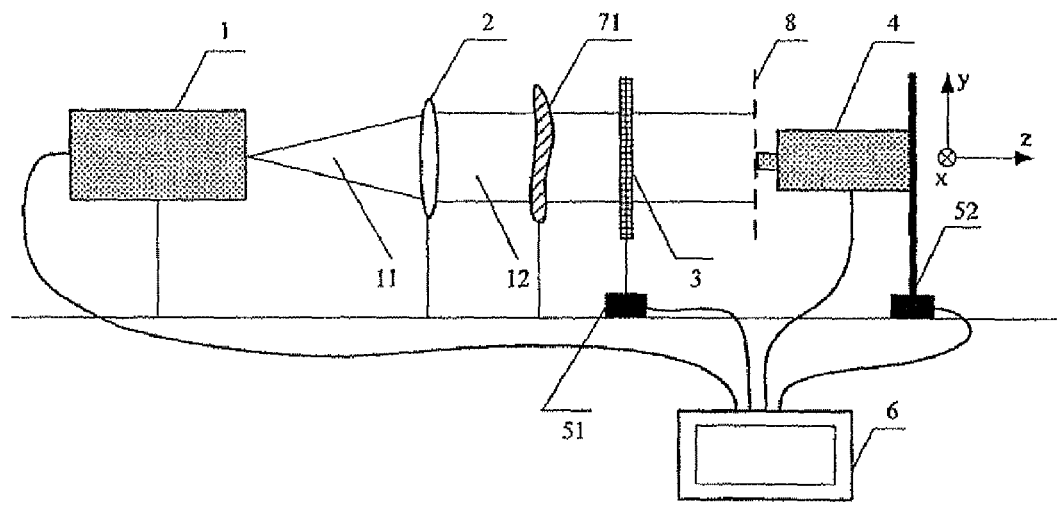
FIG. 1 is a schematic view showing the structure of an apparatus using a diffraction grating for terahertz radiation phase contrast imaging according to an embodiment of the present invention.

FIG. 1 is a schematic view (side view) showing the structure of an apparatus using a diffraction grating for transmissive terahertz radiation phase contrast imaging according to an embodiment of the present invention.

As shown in FIG. 1, the apparatus according to the embodiment of the present invention includes a continuous wave terahertz radiation emitter 1, a terahertz beam collimating lens 2, a transmissive type diffraction grating 3, a single point type continuous wave terahertz radiation detector 4, a one-dimensional translating device 51, a two-dimensional translating device 52, and a computer based data collecting and processing system 6. The data collecting and processing system 6 includes a computer, intensity image collecting software and phase contrast image generating software. The data collecting and processing system 6 controls operations of the whole apparatus, reads an output signal from the detector to obtain an intensity distribution image of the parallel-beam terahertz radiation after it interacts with an object and the grating, and then retrieves a phase contrast image of the object with a phase retrieval algorithm.

The terahertz radiation emitter 1 comprises a continuous wave radiation source, such as a Backward Wave Oscillator (BWO), a Terahertz Parametric Oscillator, and a Terahertz Laser. The power of the tight source should be sufficiently high, because the terahertz wave emitted from the light source needs to be expanded for two-dimensional imaging.

The terahertz radiation detector 4 can be of a single point type, such as a Bolometer, a Pyroelectric Detector, and Golay Cells. The terahertz radiation detector 4 can also be of an array type, such a Microbolometer Focal-Plane Array Camera.

The diffraction grating 3 can be of a transmissive or reflective type. For a transmissive diffraction grating, materials for the grating may be selected among materials that have a good transmittance for the tera hertz radiation, such as high-resistance silicon and high-density polythene (HDPE). For a reflective diffraction grating, materials therefor may be selected among materials that have a high reflectance for the terahertz radiation, such as metal.

The beam collimating lens 2 is a terahertz lens which can collimate the terahertz radiation into a parallel beam to illuminate the object and the grating, such that it is simple and easy to do the analysis of the grating diffraction and the retrieval of the phase contrast image. The beam collimating lens 2 can also be a parabolic mirror.

The continuous wave terahertz radiation generated by the continuous wave terahertz radiation emitter 1 is a divergent beam 11. The divergent beam 11 is collimated by the lens 2 into a parallel beam 12, which is incident on a sample 71 of weak absorption. The phase of the terahertz radiation passing through the sample will change. After the terahertz radiation passes through the diffraction grating 3, the phase shift information will be presented in the grating diffraction field. A detection plane 8 (in which diffraction fringes of the grating have a high contrast, and which plane can be selected through calculation by grating simulation software) parallel to the grating plane is selected, and the intensity of the terahertz radiation in the plane is measured by the single point type detector 4 in a manner of point-by-point. The intensity signal measured by the single point type detector 4 is transferred to the data collecting and processing system 6. Meanwhile, the data collecting and processing system 6 controls the two-dimensional translating device 52 to move the single point type detector 4 in the x-y plane to perform scanning, in order to obtain the periodic intensity distribution of the terahertz radiation in the plane 8.

Figure 2:
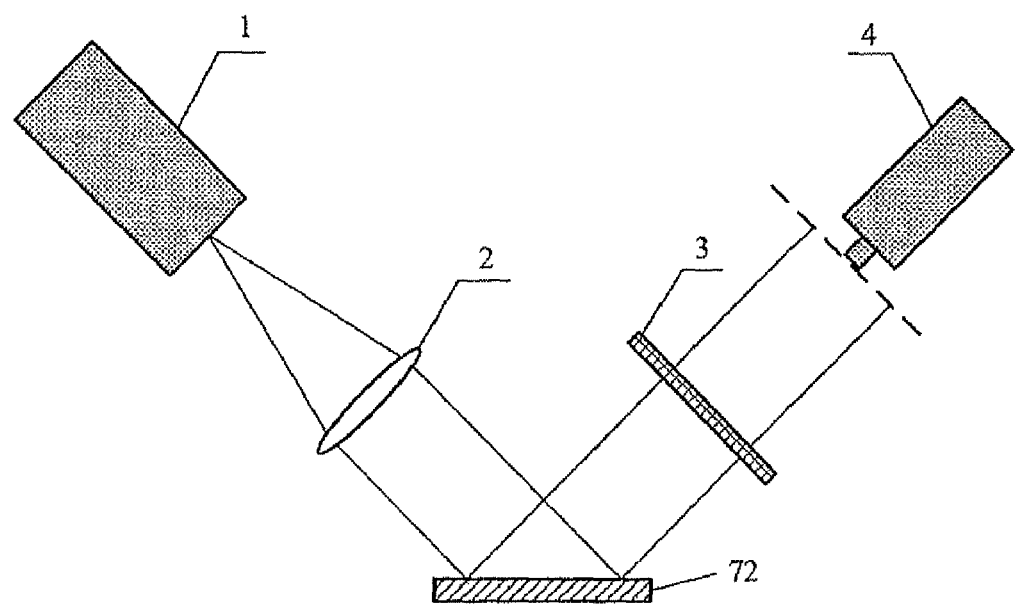
FIG. 2 shows an arrangement of the apparatus in a reflective mode according to an embodiment of the present invention.

The above description is about the operation of the apparatus in a transmissive mode. According to another embodiment of the present invention, a reflective mode is also possible. As shown in FIG. 2, the terahertz beam collimated by the lens 2 is incident on the surface of the object 72. The single point type detector 4 measures the periodic intensity distribution of the reflected wave after passing through the grating. The terahertz wave has a varied phase when being reflected by the object 72 with respect to when being reflected by a reference plan (such as a metal mirror) which is disposed instead of the object 72, due to the surface profile and complex refractive index of the object. The phase variation information will also be presented in the grating diffraction field. The reflective mode is usually used for imaging of an object opaque to the terahertz radiation.

Figure 3:
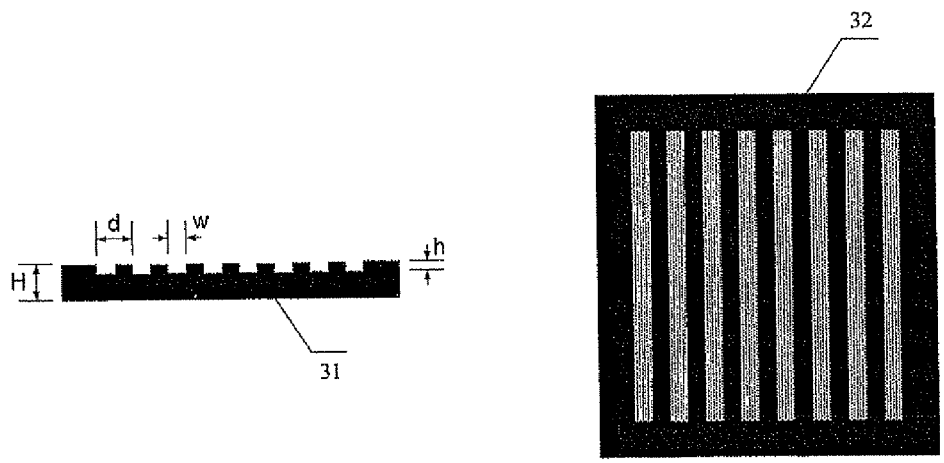
FIG. 3 is a schematic view showing the structure of the diffraction grating in the apparatus according to an embodiment of the present invention.
Figure 4:
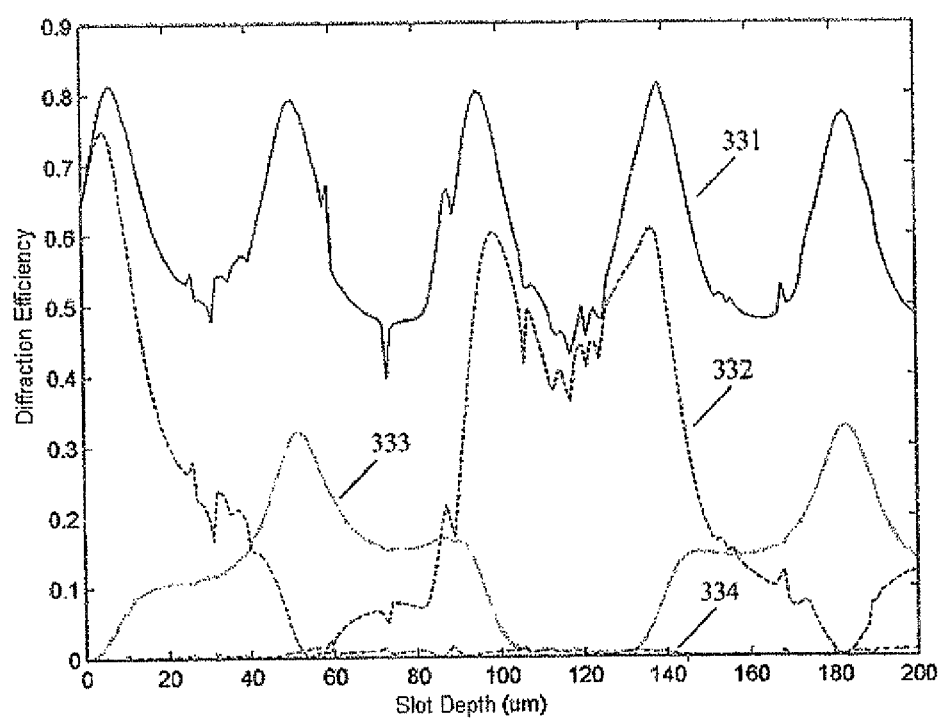
FIG. 4 shows a total transmittance curve and relative diffraction efficiency curves when the grating has a total thickness of 360 μm and a slot depth between 0-200 μm.

FIG. 3 shows the structure of the diffraction grating used in the apparatus according to an embodiment of the present invention. FIG. 3 shows its front view 31 and top view 32. Having the knowledge about the frequency of the terahertz radiation source, parameters of the grating, such as material, period, duty cycle, slot depth, and thickness, are designed to obtain desirable diffraction characteristics, such as proper diffraction angle, and sufficiently high diffraction efficiency. As illustrated above, the grating may be disposed in a near or far field behind the object. In manufacturing the grating, rectangular slots with a depth of h, a width of w, and a period of d are etched in a silicon substrate with a thickness of H. These dimensions are mainly determined by taking into consideration factors such as diffraction efficiency, energy distribution among respective diffraction orders and diffraction angle. There is no restrictive requirement on the thickness H of the silicon substrate as long as it is easy to be processed. The period d determines the number of the diffraction orders and the diffraction angle. In order to generate a diffraction field with a periodic intensity distribution, there must be a non-$0^{th}$ order diffraction. The duty cycle is usually selected to be 0.5, i.e. w=d/2. When the above parameters are determined, the slot depth h will determine the diffraction efficiency of each order. Assuming that the wavelength is 300 μm (at a frequency of 1 THz), a monochromatic plane wave of TE polarization is normally incident on the grating. In order to generate a non-$0^{th}$ order diffraction, the period d should satisfy a condition of d>300 μm, according to the grating equation. Further, as the actual width of the incident beam is limited, the fringe region is distributed in a limited range. In order to obtain a larger fringe region, the diffraction angle of the $\pm 1^{th}$ orders should be as small as possible, or in other words, the number of the diffraction orders should be as large as possible. For example, when d=2 mm, the highest order is $6^{th}$, and the diffraction angle of the $+1^{th}$ order is 8.6°. Based on the selected parameters, the diffraction efficiencies of each order at different slot depths are calculated. FIG. 4 shows a total transmittance curve (331) and diffraction efficiency curves of order 0 (332), orders ±1 (333), and orders ±2 (334) in the case where H=360 μm and h varies between 0 and 200 μm. It can be seen that in order to achieve sufficiently high total transmittance and diffraction efficiencies at non-$0^{th}$ orders (orders ±1), the proper slot depth may be about 52 μm or 183 μm.

Next, a phase information retrieval method will be illustrated with reference to the transmissive phase contrast image system.

For a phase object of no absorption, the intensity of the terahertz radiation does not change after it passes through the object. Therefore, direct imaging is impossible. However, if a grating is disposed behind the object, the phase variation of the terahertz radiation caused by the object leads to the intensity variation of the grating diffraction field. Such intensity information then may be captured by a normal detector. If the diffraction characteristic of the grating is known, the phase shift of the incident field can be derived from the intensity distribution of the diffraction field.

The phase shift can be calculated according to the grating diffraction theory. If the terahertz radiation has a wavelength of λ which is much less than the grating period d (e.g. λ/d<0.1), the scalar theory is applicable. If λ is close to d, then the vector theory is applicable. Take the former case as an example, assuming a monochromatic plane wave with a wavelength λ is normally incident on the grating (the definition of the coordinate system is shown in FIG. 1), the intensity distribution of the transmission field is:

$$I(x, y, z) = \sum_m a_m(z)\exp(imKx) \text{ wherein } a_m(z) = \sum_n \beta_{m+n}(z)\beta_n^*(z), \quad (1)$$

$$\beta_n = t_n \exp\left(-i\pi\lambda z \frac{n^2}{d^2}\right), \quad K = \frac{2\pi}{d}$$

is the wave vector of the grating, and $t_n$ is the Fourier expansion coefficient of the transfer function of the grating. If there is a phase object in front of the grating, the phase of the terahertz radiation will be shifted after the terahertz radiation passes through the object (as for the reflective mode, the phase distribution of the terahertz radiation changes after the terahertz radiation is reflected by the object). Assuming that the phase shift distribution is Φ(x,y), the intensity distribution of the grating transmission field is:

$$I(x, y, z) \approx \sum_m a_m(z)\exp\{imK[x - z\varphi(x, y)]\} \quad (2)$$

$$\text{wherein } \varphi(x, y) = \frac{\lambda}{2\pi}\frac{\partial \Phi(x, y)}{\partial x}.$$

In the distance of one period, the grating is translated at equivalent pitches along the direction of its wave vector by means of the translating device 51. The intensity distribution in the detection plane at each position of the grating is collected, which is used by the data collecting and processing system 6 to derive the phase shift according to equation (2). Then the phase contrast image of the object can be plotted.

For example, the translating device 51 translates the grating along the direction of the wave vector of the grating within the distance of one period. For each particular position of the grating, in the grating diffraction field a plane, in which the contrast of the diffraction fringes is high, is selected. The intensity distribution of the terahertz radiation may be measured by the single point type detector 4 point by point in a manner of raster scanning, or this two-dimensional signal may be directly measured by an array detector.

After that, the data collecting and processing system 6 retrieves the phase distribution (that is, the phase shift of the terahertz radiation caused by the object) of the grating incident field in the plane perpendicular to the incident direction from the measured periodic intensity pattern and the diffraction characteristic of the grating, in order to create the phase contrast image of the object.

The above description is only for illustrating embodiments of the present invention. Those skilled in the art will understand that any modifications or partial substitutions that do not depart from the scope of the present invention fall within the scope of the invention defined by the attached claims. Therefore, the scope of the present invention is defined by the claims.

What is claimed is:

1. A method for phase contrast imaging using a diffraction grating, comprising steps of:
    illuminating an object by terahertz radiation such that the terahertz radiation interacts with the object;
    illuminating the grating by the terahertz radiation that has interacted with the object;
    translating the diffraction grating along the direction of the grating wave vector, to measure, for each of the different grating positions, an intensity distribution of the terahertz radiation that has interacted with the object and with the grating in a diffraction field; and
    retrieving a phase contrast image of the object from the intensity distributions.

2. The method according to claim 1, wherein the step of illuminating the grating by the terahertz radiation that has interacted with the object comprises:
    illuminating the grating by the terahertz radiation that has passed through the object.

3. The method according to claim 1, wherein the step of illuminating the grating by the terahertz radiation that has interacted with the object comprises:
    illuminating the grating by the terahertz radiation that has been reflected by the object.

4. The method according to claim 1, wherein the diffraction grating is translated within a distance of one period along the direction of the grating wave vector, such that for each particular grating position, a plane in the diffraction field of the grating, in which a contrast of diffraction fringes is relatively high, is selected for measuring the intensity distribution of the terahertz radiation.

5. The method according to claim 4, wherein the intensity distribution of the terahertz radiation is measured point by point by a single point type detector in a manner of raster scanning.

6. The method according to claim 4, wherein the intensity distribution of the terahertz radiation is measured directly by an array detector.

7. The method according to claim 1, wherein the step of retrieving the phase contrast image of the object from the intensity distributions comprises:
    retrieving a phase distribution of a grating incident field in a plane perpendicular to an incident direction from the periodic intensity pattern and diffraction characteristic of the grating; and
    creating the phase contrast image of the object from the phase distribution.

8. An apparatus for phase contrast imaging, comprising:
    a terahertz radiation emitter for generating terahertz radiation, which illuminates an object to interact with the object;
    a diffraction grating, which is illuminated by the terahertz radiation that has interacted with the object;
    a terahertz radiation detector for measuring, for each of different grating positions, an intensity distribution of the terahertz radiation that has interacted with the object and with the grating in a diffraction field; and
    a data collecting and processing system for retrieving a phase contrast image of the object from the intensity distributions.

9. The apparatus for phase contrast imaging according to claim 8, further comprising:
    a collimating portion arranged at an output side of the terahertz radiation emitter for collimating the terahertz radiation into a parallel beam.

10. The apparatus for phase contrast imaging according to claim 9, wherein the collimating portion is a terahertz lens or a parabolic mirror.

11. The apparatus for phase contrast imaging according to claim 8, further comprising:
    a translating device for translating the grating at equivalent pitches along the direction of the grating wave vector.

12. The apparatus for phase contrast imaging according to claim 11, wherein the translating device translates the diffraction grating within a distance of one period along the direction of the grating wave vector, such that for each particular grating position, a plane in the diffraction field of the grating, in which a contrast of diffraction fringes is relatively high, is selected for measuring the intensity distribution of the terahertz radiation by the terahertz radiation detector.

13. The apparatus for phase contrast imaging according to claim 12, wherein the terahertz radiation detector is a single point type detector for measuring the intensity distribution of the terahertz radiation point by point in a manner of raster scanning.

14. The apparatus for phase contrast imaging according to claim 12, wherein the terahertz radiation detector is an array detector for measuring the intensity distribution of the terahertz radiation directly.

15. The apparatus for phase contrast imaging according to claim 8, wherein the data collecting and processing system retrieves a phase distribution of a grating incident field in a plane perpendicular to an incident direction from the periodic intensity pattern and diffraction characteristic of the grating, and creates the phase contrast image of the object from the phase distribution.

* * * * *